US011963685B2

(12) United States Patent
Muhlenkamp et al.

(10) Patent No.: US 11,963,685 B2
(45) Date of Patent: Apr. 23, 2024

(54) ESOPHAGUS SIZING INSTRUMENT

(71) Applicant: Cilag GmbH International, Zug (CH)

(72) Inventors: Tylor C. Muhlenkamp, Cincinnati, OH (US); Kevin M. Fiebig, Cincinnati, OH (US); David K. Norvell, Monroe, OH (US)

(73) Assignee: Cilag GmbH International, Zug (CH)

(*) Notice: Subject to any disclaimer, the term of this patent is extended or adjusted under 35 U.S.C. 154(b) by 924 days.

(21) Appl. No.: 16/506,018

(22) Filed: Jul. 9, 2019

(65) Prior Publication Data
US 2021/0007752 A1 Jan. 14, 2021

(51) Int. Cl.
*A61B 5/107* (2006.01)
*A61B 5/00* (2006.01)
(Continued)

(52) U.S. Cl.
CPC ........ *A61B 17/12099* (2013.01); *A61B 5/107* (2013.01); *A61B 5/1076* (2013.01); *A61B 5/6856* (2013.01); *A61B 17/221* (2013.01); *A61B 90/06* (2016.02); *A61B 5/1077* (2013.01); *A61B 2017/00827* (2013.01); *A61B 2017/00876* (2013.01); *A61B 17/12013* (2013.01); *A61B 2017/1205* (2013.01); *A61B 2090/061* (2016.02)

(58) Field of Classification Search
CPC ............................. A61B 5/1076; A61B 5/6856
See application file for complete search history.

(56) References Cited

U.S. PATENT DOCUMENTS 6,599,265 B2 * 7/2003 Bon .................. A61M 25/0136
604/95.04
7,175,589 B2    2/2007 Deem et al.
(Continued)

FOREIGN PATENT DOCUMENTS

EP           1339321 B1 * 10/2011  ........... A61B 5/1076
WO    WO-9745061 A1 * 12/1997  ......... A61F 9/00763
(Continued)

OTHER PUBLICATIONS

International Search Report and Written Opinion dated Sep. 18, 2020 for Application No. PCT/IB2020/056269, 12 pgs.
(Continued)

*Primary Examiner* — Charles A Marmor, II
*Assistant Examiner* — Raymond P Dulman
(74) *Attorney, Agent, or Firm* — Frost Brown Todd LLP

(57) ABSTRACT

An apparatus includes a handle assembly, a shaft assembly, and an end effector. The handle assembly includes a body and an actuator. The actuator includes a rotary member that is configured to be driven by a finger of a hand that grasps the handle body. The shaft assembly includes an external sheath that is fixed to the handle body and an inner shaft that is coupled to the actuator. The inner shaft is configured to slide longitudinally relative to the external sheath in response to rotation of the first rotary member relative to the handle body. The end effector is configured to encompass a bodily lumen and includes a flexible member extending distally from the inner shaft. A first coupling element is fixed to the distal tip of the flexible member. A second coupling element is fixed to the external sheath. The flexible member defines an adjustable loop.

18 Claims, 17 Drawing Sheets

(51) Int. Cl.
  *A61B 17/12* (2006.01)
  *A61B 17/221* (2006.01)
  *A61B 90/00* (2016.01)
  *A61B 17/00* (2006.01)

(56) References Cited

U.S. PATENT DOCUMENTS

| | | | |
|---|---|---|---|
| 7,695,427 B2 | 4/2010 | Kugler et al. | |
| 8,070,670 B2 | 12/2011 | Deem et al. | |
| 8,486,082 B2 | 7/2013 | Geisert et al. | |
| 8,585,747 B2 | 11/2013 | Andreas et al. | |
| 8,734,475 B2 | 5/2014 | Ekvall et al. | |
| 10,449,073 B1 * | 10/2019 | Longo | A61F 2/95 |
| 10,828,064 B2 | 11/2020 | Flakne et al. | |
| 2002/0111567 A1 * | 8/2002 | Vanden Hoek | A61B 5/107 |
| | | | 600/587 |
| 2011/0077621 A1 * | 3/2011 | Graham | A61M 39/1011 |
| | | | 604/528 |
| 2012/0041261 A1 * | 2/2012 | Shunsuke | A61B 1/00082 |
| | | | 600/115 |
| 2012/0061447 A1 * | 3/2012 | Williams | A61B 17/115 |
| | | | 227/175.1 |
| 2012/0277582 A1 * | 11/2012 | Mafi | A61B 17/8811 |
| | | | 600/431 |
| 2013/0345801 A1 * | 12/2013 | Conklin | A61F 2/243 |
| | | | 623/2.11 |
| 2014/0336744 A1 * | 11/2014 | Tani | A61F 2/966 |
| | | | 623/1.11 |
| 2015/0157401 A1 * | 6/2015 | Falwell | A61B 5/6856 |
| | | | 606/41 |
| 2017/0065209 A1 * | 3/2017 | Radl | A61B 5/1076 |
| 2018/0168672 A1 * | 6/2018 | Chu | A61B 17/221 |
| 2019/0029689 A1 | 1/2019 | Shelton, IV et al. | |
| 2019/0269436 A1 * | 9/2019 | Flakne | A61B 17/2909 |

FOREIGN PATENT DOCUMENTS

| | | |
|---|---|---|
| WO | WO 2010/111592 A1 | 9/2010 |
| WO | WO 2011/116208 A1 | 9/2011 |
| WO | WO 2013/176993 A1 | 11/2013 |
| WO | WO 2017/019653 A1 | 2/2017 |

OTHER PUBLICATIONS

US Design U.S. Appl. No. 29/697,469, entitled "Esophagus Sizing Instrument," filed Jul. 9, 2019.

* cited by examiner

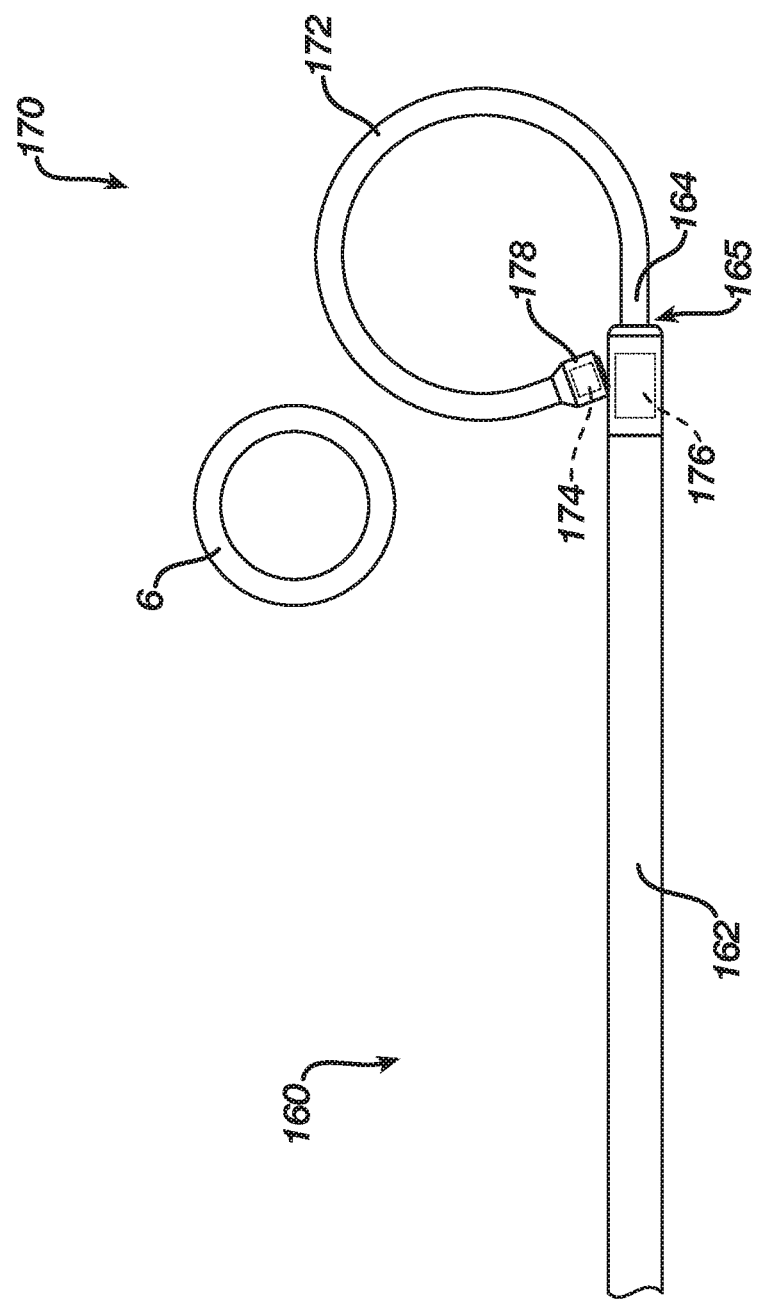

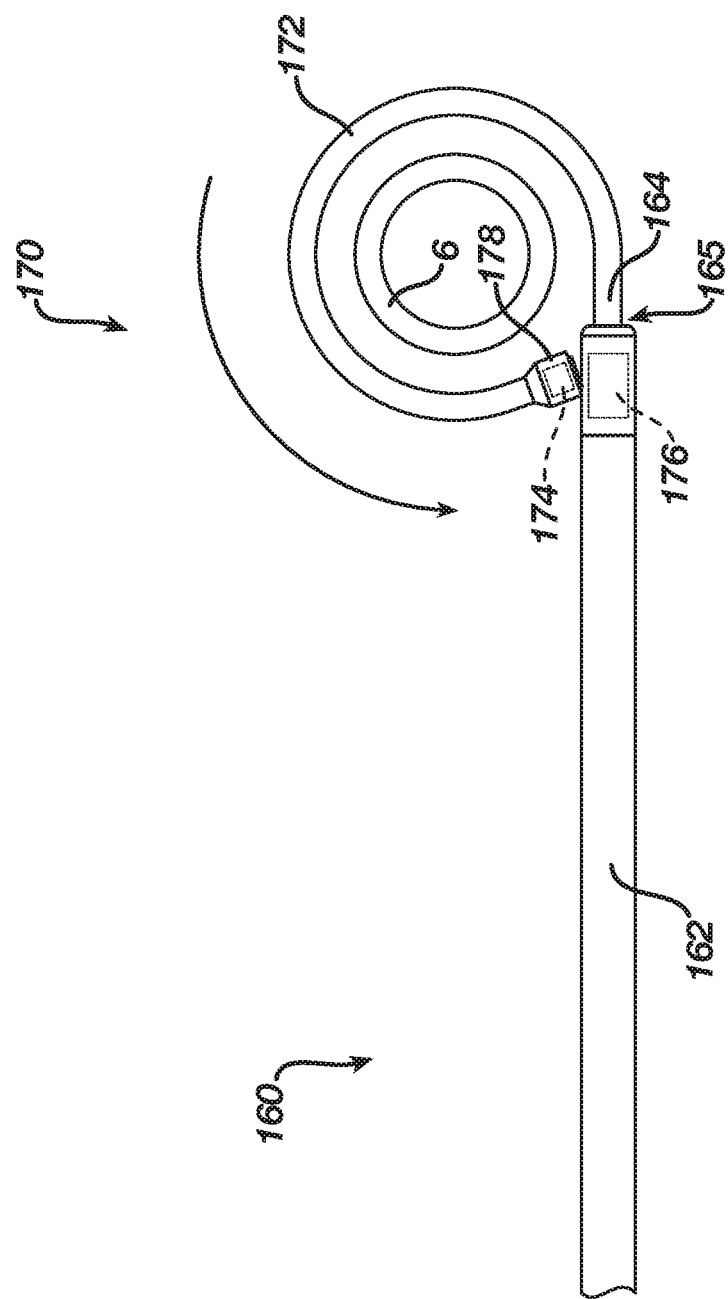

1

ESOPHAGUS SIZING INSTRUMENT

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease (or "GERD"), which effects the esophagus.

A normal, healthy, esophagus is a muscular tube that carries food from the mouth, through the chest cavity and into the upper part of the stomach. A small-valved opening in the esophagus, called the lower esophageal sphincter (or "LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes of the stomach relative to the lower esophagus; or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; and U.S. Pat. No. 8,734,475, entitled "Medical Implant with Floating Magnets," issued May 27, 2014, the disclosure of which is incorporated by reference herein.

While various kinds and types of instruments have been made and used to treat or otherwise engage anatomical lumens, it is believed that no one prior to the inventors has made or used an invention as described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 14A depicts a top plan view of the end effector and shaft assembly of FIG. 10 placed adjacent to a lower esophageal sphincter, where the end effector is in a distal, closed, position;

FIG. 14C depicts a top plan view of the end effector and shaft assembly of FIG. 10, where the end effector is in the distal, closed, position while the end effector surrounds the lower esophageal sphincter.

Figure 1:
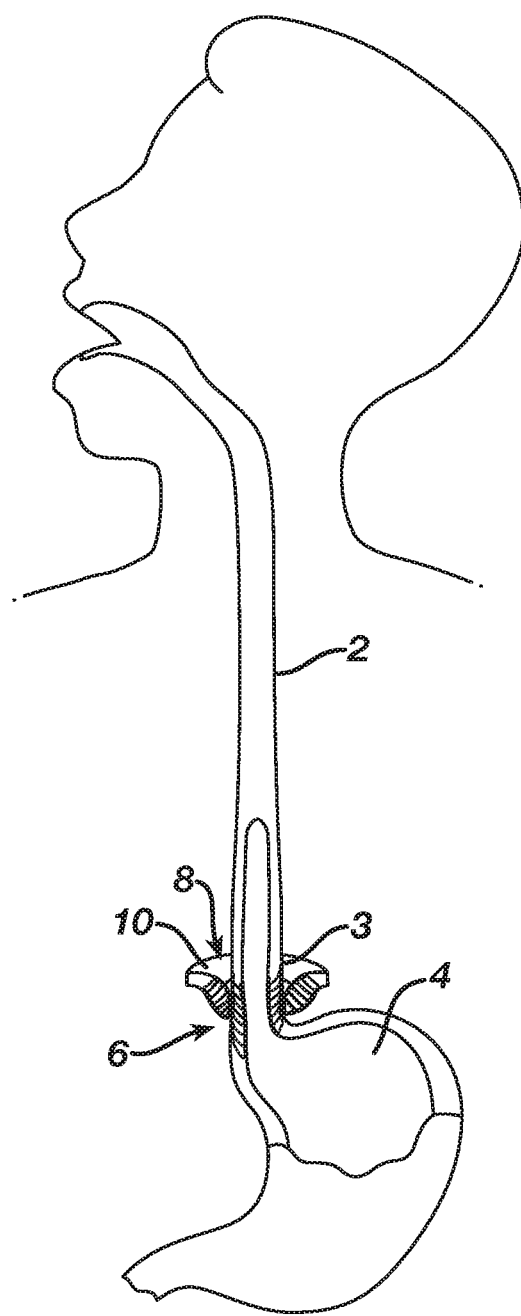
FIG. 1 depicts a cross-sectional side view, taken along a coronal plane of the body, of a biological passage.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. OVERVIEW

Figure 2:
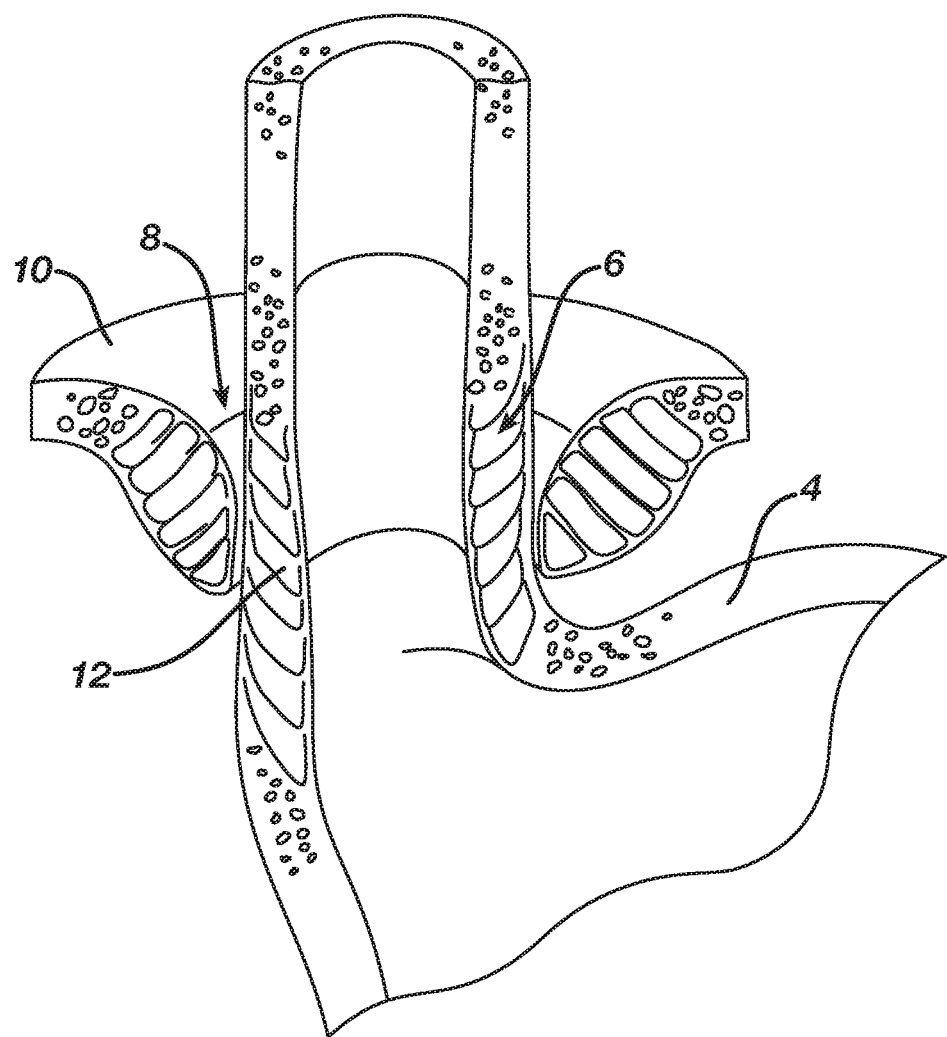
FIG. 2 depicts a cross-sectional isometric view, taken along a coronal plane of the body, of a human esophagogastric junction.

FIGS. 1-2 show selected portions of human anatomy, which includes an esophagus (2) extending from the mouth, through a hiatus (8) defined by a diaphragm (10), and into a stomach (4). The esophagus (2) also includes a distal esophagus (3) and an LES (6). The LES (6) is located along distal esophagus (3) adjacent to the junction of the esophagus (2) and the stomach (4). The portion of the LES (6) extending through the hiatus (8) is supported by the diaphragm (10). When functioning properly, the LES (6) is configured to transition between an occluded state and an opened state (as shown in FIG. 2). As best seen in FIG. 2, the LES (6) includes a plurality of sling fibers (12). The sling fibers (12) are smooth muscle tissue that may help regulate the LES (6) transitioning between the occluded state and the open state. The hiatus (8) of the diaphragm (10) may also help the LES (6) transition between the occluded state and the open state.

A healthy LES (6) transitions between the occluded state and the opened state in order to act as a valve. In other words, a healthy LES (6) may transition from the occluded state to the opened state in order to allow solids, liquids, and/or gasses to selectively travel between the esophagus (2) and the stomach (4). For example, a healthy LES (6) may transition from the occluded state to the opened state to permit a bolus of food to travel from the esophagus (2) into the stomach (4) during peristalsis; or to vent intra-gastric pressure from the stomach (4) toward the esophagus (2). Additionally, in the occluded state, a healthy LES (6) may prevent digesting food and acidic fluid from exiting stomach (4) back into the esophagus (2).

If the LES (6) ceases functioning properly by prematurely relaxing, and thereby improperly transitioning the esophagus (2) from the occluded state to the opened state, undesirable consequences may occur. Examples of such undesirable consequences may include acidic reflux from the stomach (4) into the esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant around a malfunctioning LES (6) such that the implant and/or the LES (6) may properly transition between the occluded state and the opened state.

Such an implant may include a circumferential array of magnetic elements that are magnetically attracted toward adjacent magnetic elements. Such magnetic elements may expand and contract relative to each other while encompassing the exterior of a malfunctioning LES (6). Therefore, the magnetic attraction between adjacent magnetic elements may help a malfunctioning LES (6) properly remain in an occluded state; while the ability for magnetic elements to expand and contract relative to each other may allow an LES (6) to suitably transition into the opened state. While magnetic elements are used to bias a malfunctioning LES (6) toward an occluded state while also allowing a malfunctioning LES (6) to suitably transition into an open state, any other type of biasing elements may be used as would be apparent to one having ordinary skill in the art in view of the teachings herein. Merely illustrative examples of implants that may be used to encompass the exterior of a malfunctioning LES (6) are disclosed in U.S. Pat. No. 7,695,427, the disclosure of which is incorporated by reference herein and U.S. Pub. No. 2019/0029689, entitled "Method for Assisting a Sphincter," published Jan. 31, 2019, the disclosure of which is incorporated by reference herein.

II. EXEMPLARY SIZING INSTRUMENT

As mentioned above, certain implants may encompass a malfunctioning LES (6) within the body to suitably assist such sphincters in properly transitioning between the occluded state and the open state. Since the diameter of the LES (6) may vary from patient to patient, it may be necessary or otherwise desirable to vary the length of an implant, to correspond with the diameter of the LES (6) of the patient at hand, to thereby maximize the likelihood of a successful outcome. The suitable length of an implant (e.g., circumference of an implant when attached to the outer diameter of the LES (6)) may be determined by measuring the outer diameter of the LES (6) of the patient at hand. For instance, if an implant includes an array of magnetic elements, the number of magnetic elements used for a specific implant may be determined by the outer diameter of the LES (6). The larger the outer diameter, the more magnetic elements will be used; and the smaller the outer diameter, the less magnetic elements will be used.

Since the outer diameter of the LES (6) may vary depending on the patient, and this may influence the configuration of an implant that is to be placed around the LES (6), it may be desirable to use a sizing instrument having an end effector that is configured to encompass and measure an outer diameter of an LES (6) of an individual patient. An operator may utilize the measurement of the LES (6) to determine what size implant should be used for an individual patient. Upon identifying the appropriate size of the implant, the operator may select the appropriately sized implant from a plurality of available implants. Alternatively, the operator may modify the length of an implant to achieve the appropriate size.

The following describes an exemplary sizing instrument (100) that may be utilized to provide a proper engagement between an end effector (170) of sizing instrument (100) and the outer diameter of the LES (6). While sizing instrument (100) is described herein in the context of measuring the LES (6) of the esophagus (2), variations of sizing instrument (100) may be used to measure the outer circumference of any other anatomical passageway, including but not limited to the pylorus, the intestinal region surrounding the ileocecal sphincter, a passageway associated with the sphincter of Oddi, a region of a urethra surrounding the urethral sphincter, a region of the rectum, a region surrounding the upper esophageal sphincter, or any other anatomical passageway.

Figure 3:
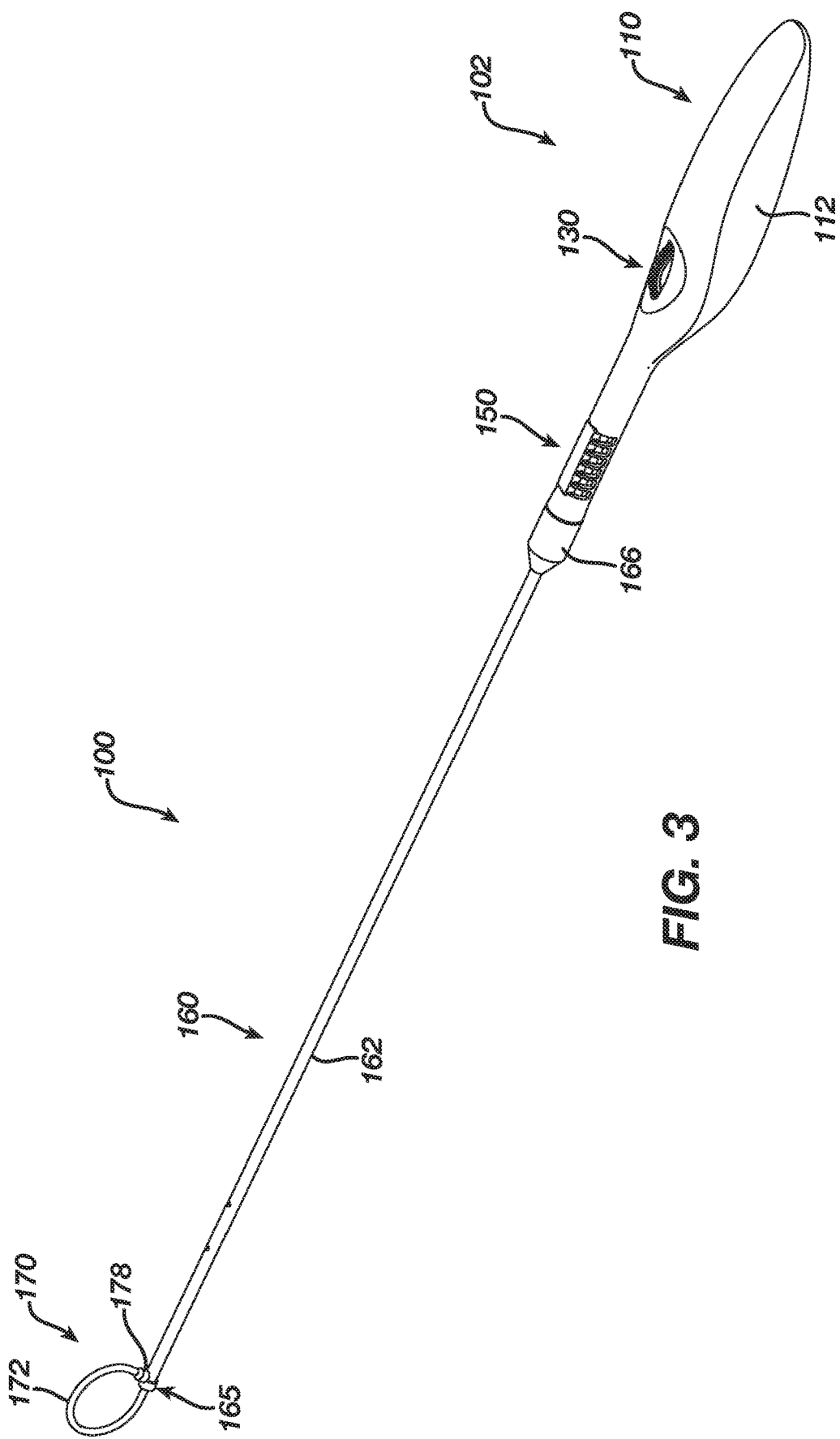
FIG. 3 depicts a perspective view of an exemplary sizing instrument that may be used to measure the biological passage of FIG. 1.
Figure 4:
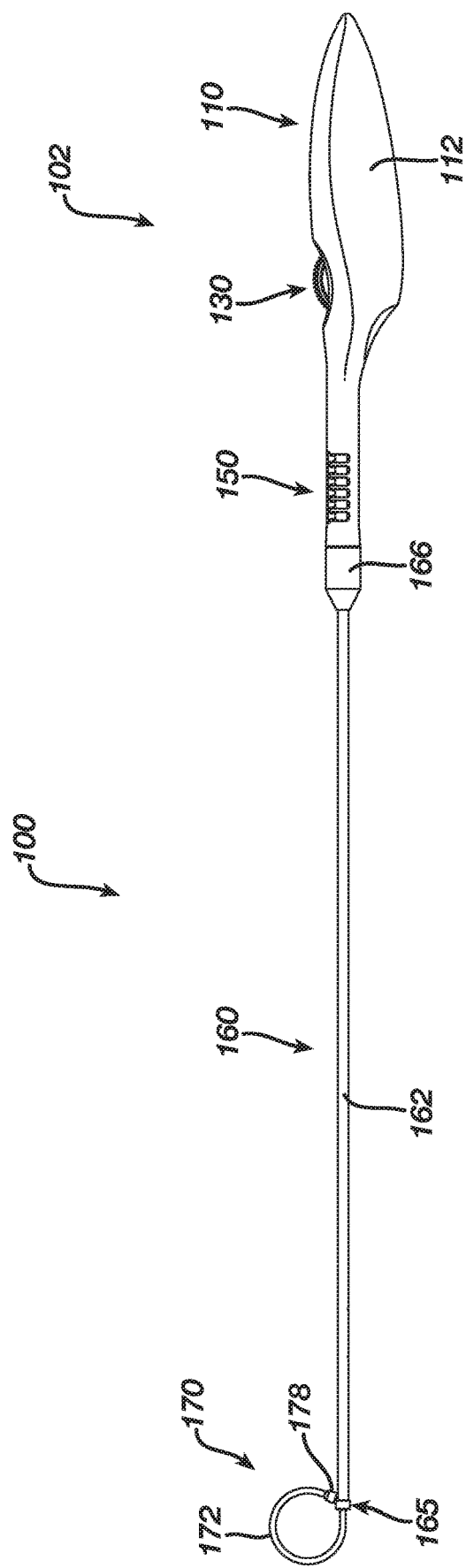
FIG. 4 depicts a side elevation view of the instrument of FIG. 3.

As shown in FIGS. 3-4, sizing instrument (100) of the present example includes a handle assembly (102), a shaft assembly (160) extending distally from handle assembly (102), and an end effector (170) extending distally from shaft assembly (160).

Figure 5:
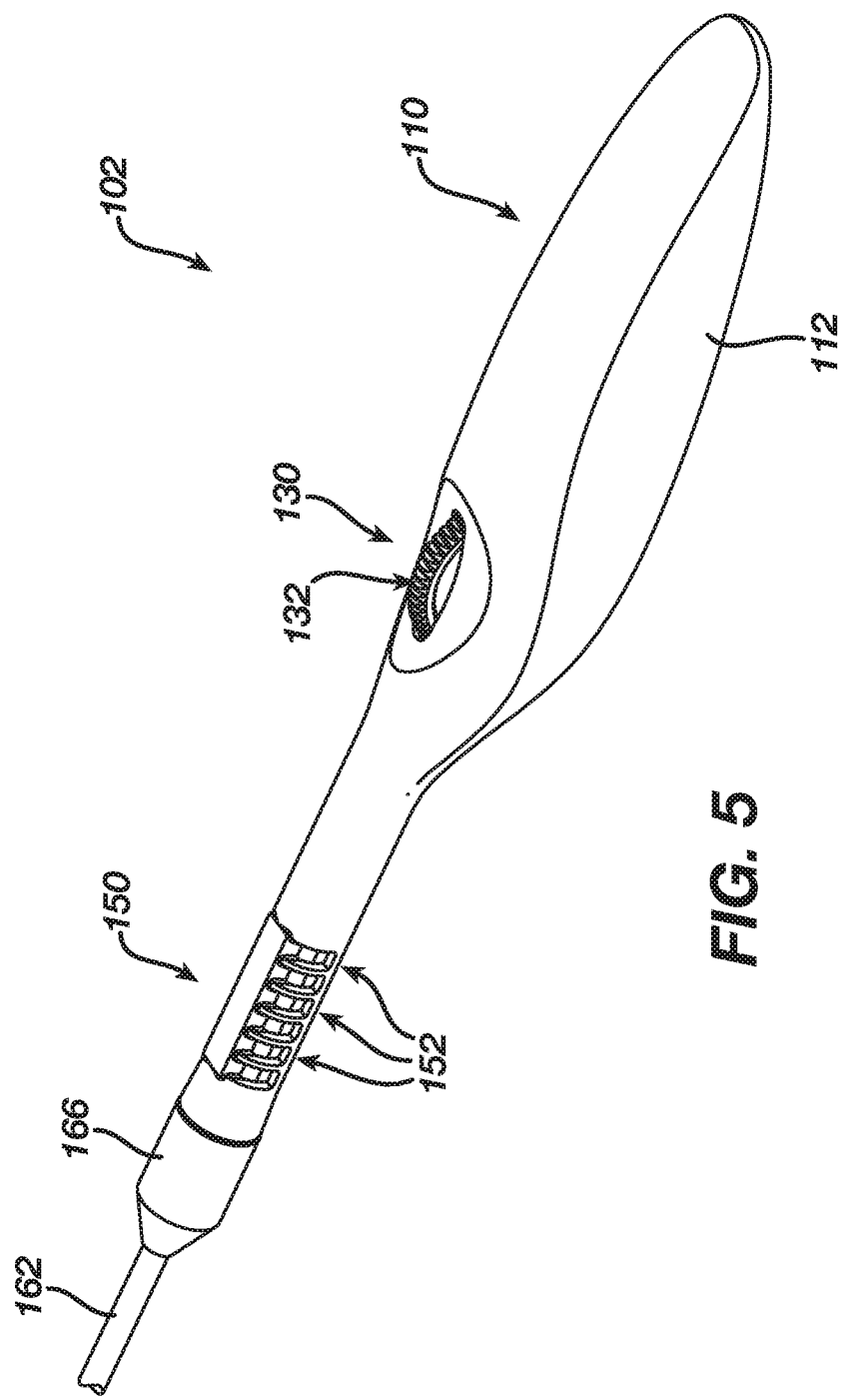
FIG. 5 depicts a perspective view of a handle assembly of the instrument of FIG. 3.
Figure 6:
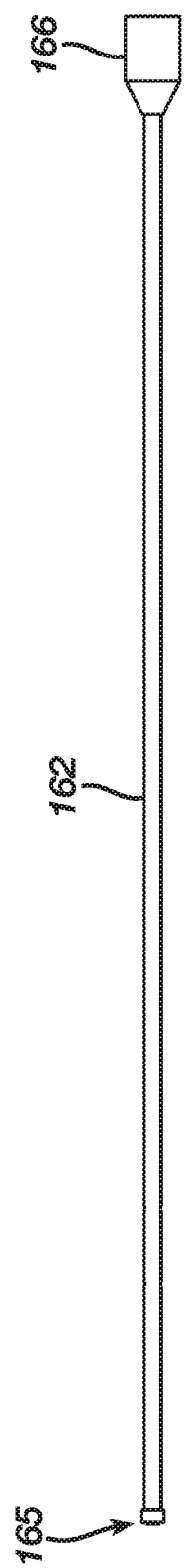
FIG. 6 depicts a side elevation view of an outer sheath of a shaft assembly of the instrument of FIG. 3.
Figure 7:
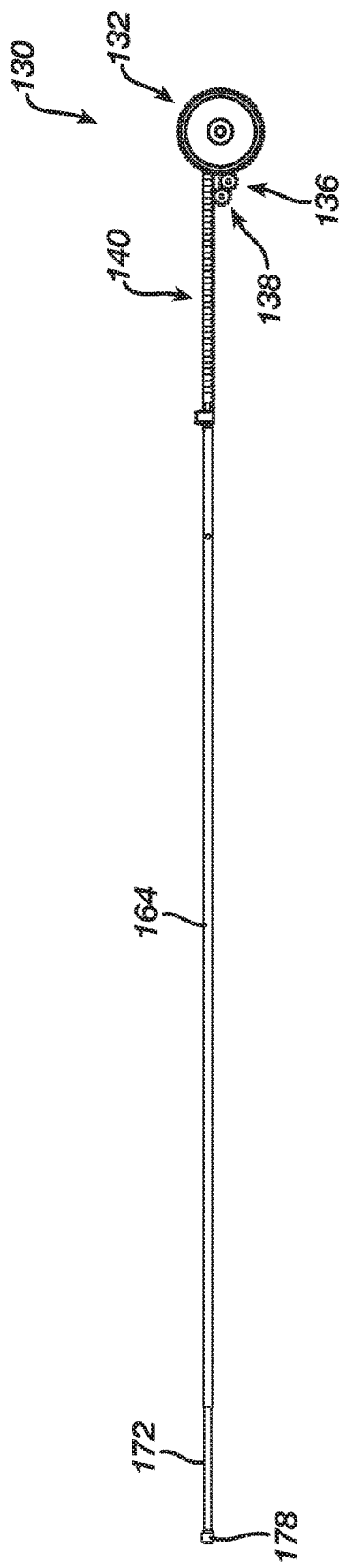
FIG. 7 depicts a side elevation view of an inner shaft of the shaft assembly of the instrument of FIG. 3, with an associated actuation assembly.
Figure 8:
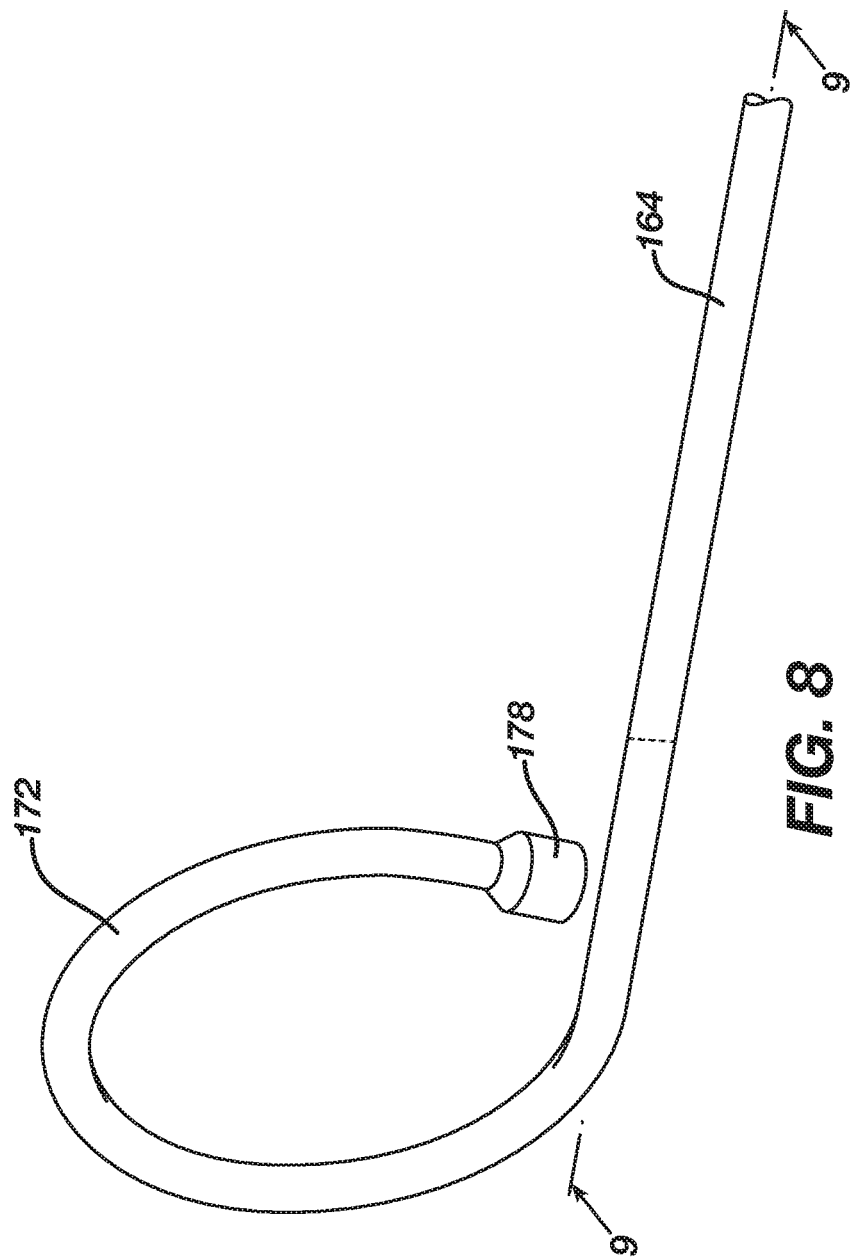
FIG. 8 depicts a perspective view of the inner shaft of FIG. 7.
Figure 9:
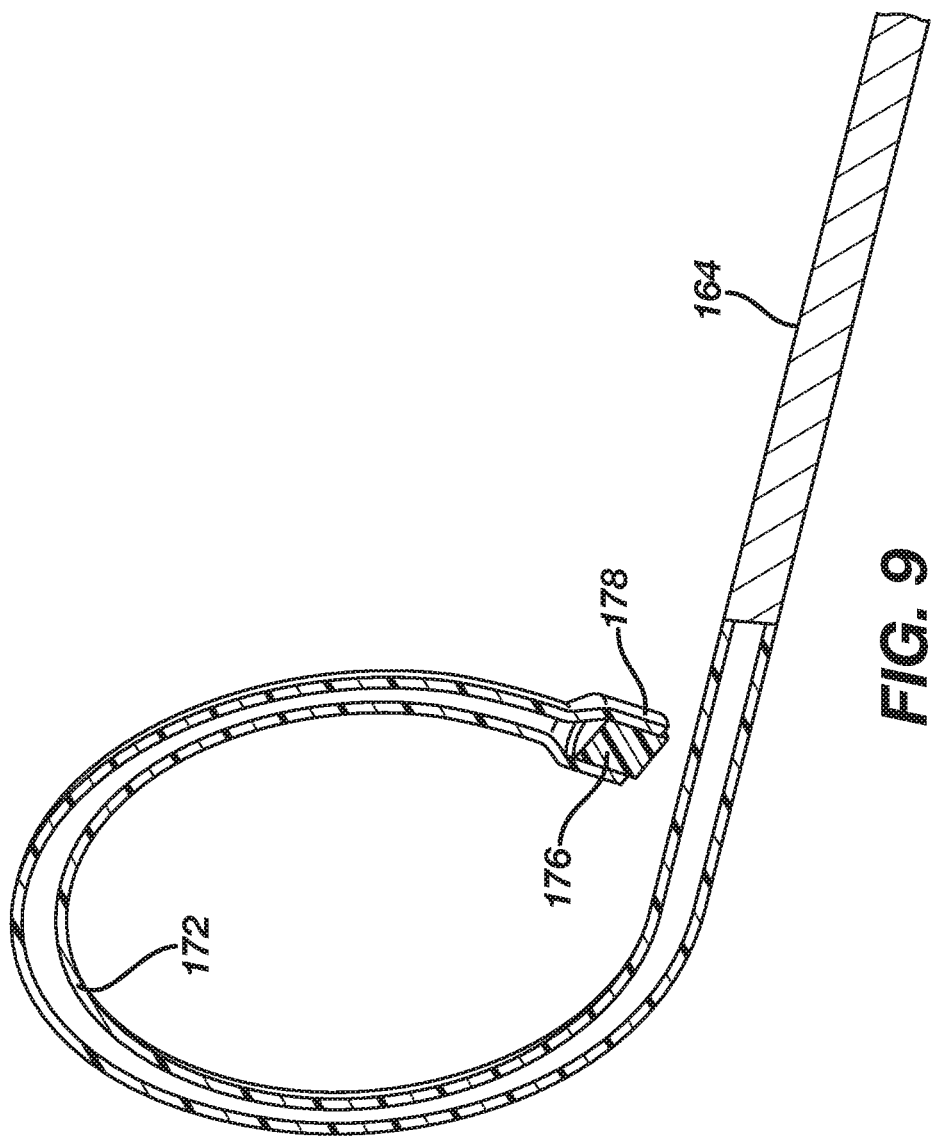
FIG. 9 depicts a cross-sectional perspective view of the inner shaft of FIG. 7, taken along line 9-9 of FIG. 8.
Figure 10:
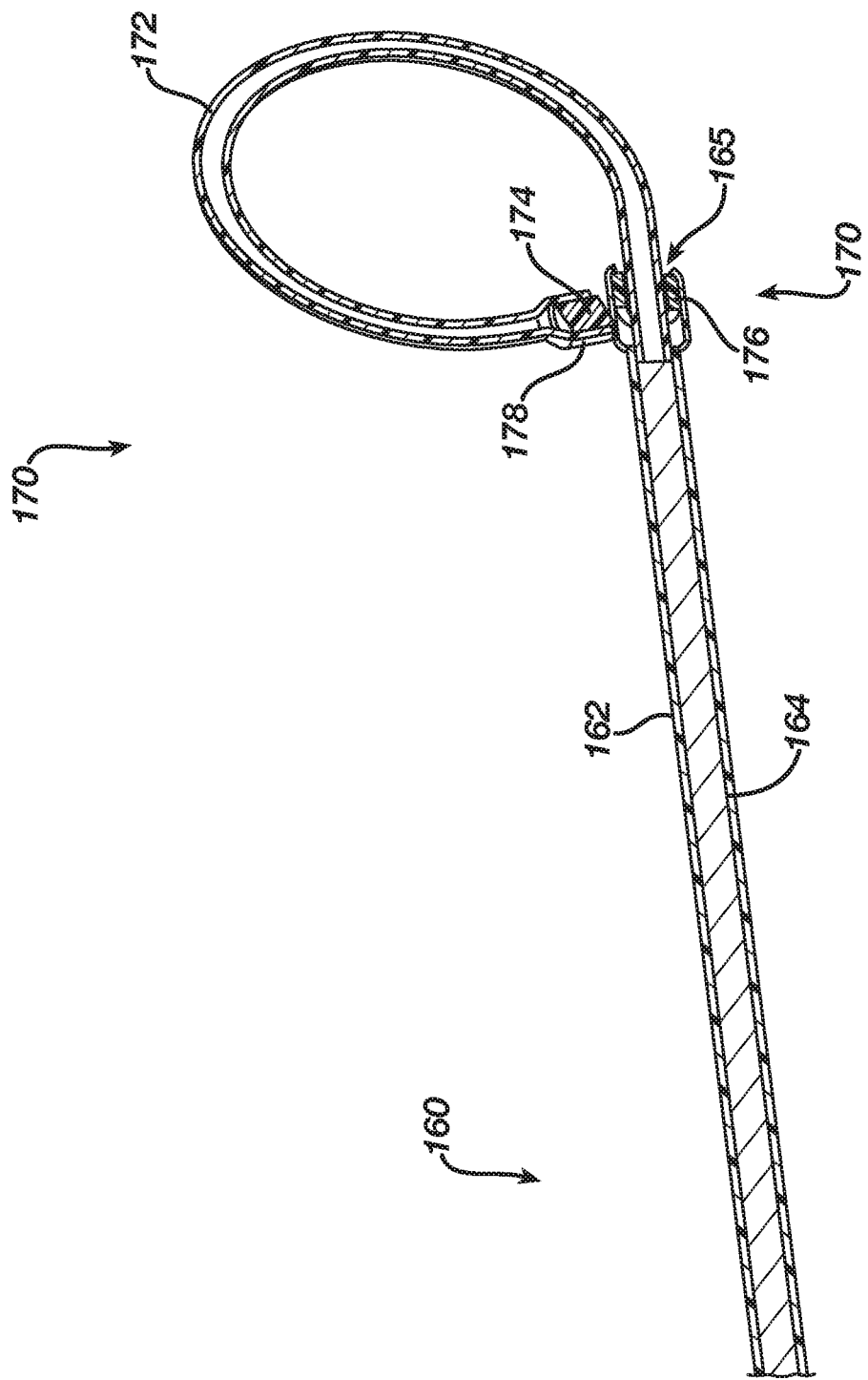
FIG. 10 depicts a cross-sectional perspective view of the shaft assembly and end effector of the instrument of FIG. 3.

As best seen in FIG. 5, handle assembly (102) includes a grip portion (110), an actuator (130), and a feedback feature (150). Grip portion (110) is formed by a housing (112) and is operable to be grasped by a single hand of an operator using a power grip. Actuator (130) includes a drive wheel (132) that is positioned to be manipulated by the thumb of the hand that grasps housing (112), such that instrument (100) may be fully operated by just one single hand of the operator. Additional components of actuator (130) will be described in greater detail below. Feedback feature (150) of the present example includes a series of windows (152) formed through housing (112), at the distal end of grip portion (110). Windows (152) are longitudinally spaced apart from each other. Each window (152) extends along a certain angular extent, such that windows (152) may be visually observed by an operator looking from either side of handle assembly (102). As will be described in greater detail below, an indicator (146) of actuator (130) is observable through windows (152) in order to discern the size of an LES (6) that is being measured by instrument (100). Windows (152) are formed on each side of handle assembly (102), such that the operator may readily observe windows (152) regardless of which side of handle assembly (102) the operator's eyes are facing. Also in the present example, windows (152) are simply openings without any kind of transparent cover. Thus, there is nothing that might provide a glare or otherwise make it difficult to see through windows (152) in certain procedures.

FIGS. 6-10 show components of shaft assembly (160) in greater detail. Shaft assembly (160) of this example includes an exterior sheath (162) (FIG. 6) and an inner shaft (164) (FIGS. 7 and 10) slidably housed within exterior sheath (162). Exterior sheath (162) includes an open distal end (165) and a proximal end (166) that is fixedly secured to handle assembly (102). Inner shaft (164) is fixedly secured to a rack (140) of actuator (130) as will be described in greater detail below. In the present example, exterior sheath (162) and inner shaft (164) are both rigid. By way of example only, exterior sheath (162) and inner shaft (164) may each be formed of a rigid metallic material (e.g., 304 stainless steel, 316 stainless steel, etc.) and/or a rigid polymeric material. By way of further example only, even in versions where exterior sheath (162) and inner shaft (164) are formed of a metallic material, exterior sheath (162) and inner shaft (164) may each be non-ferrous.

End effector (170) includes a resilient flexible tube (172) extending distally from inner shaft (164), a first magnet (174) (FIGS. 9 and 10) attached to a distal tip (178) of resilient flexible tube (172), and a second magnet (176) (FIG. 10) located at distal end (165) of exterior sheath (162). First and second magnets (174, 176) are attracted to each other such that distal tip (178) of resilient flexible tube (172) is biased toward engagement with open distal end (165) of exterior sheath (162). In some variations, distal end (165) of exterior sheath (162) simply includes a ferrous cuff or other ferrous element that is configured to magnetically couple with first magnet (174); instead of including second magnet (176). Resilient flexible tube (172) defines an adjustable loop and is resiliently biased to assume the loop configuration shown in FIGS. 3-4. While the current example includes resilient flexible tube (172), any other type of elongated resilient flexible member may be used as would be apparent to one skilled in the art in view of the teachings herein.

Figure 14B:
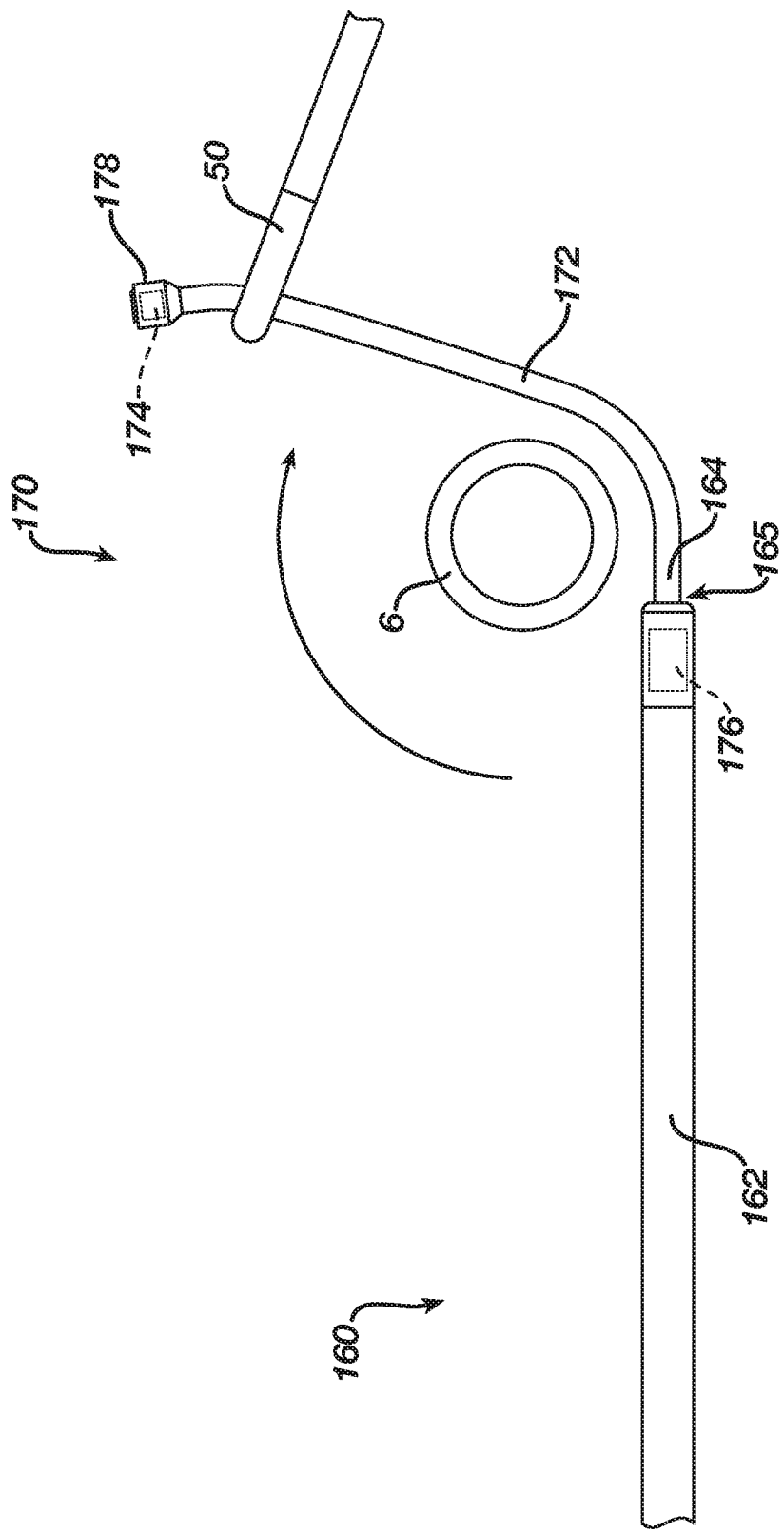
FIG. 14B depicts a top plan view of the end effector and shaft assembly of FIG. 10 placed adjacent to the lower esophageal sphincter, where the end effector is in a distal, opened, position.
Figure 14D:
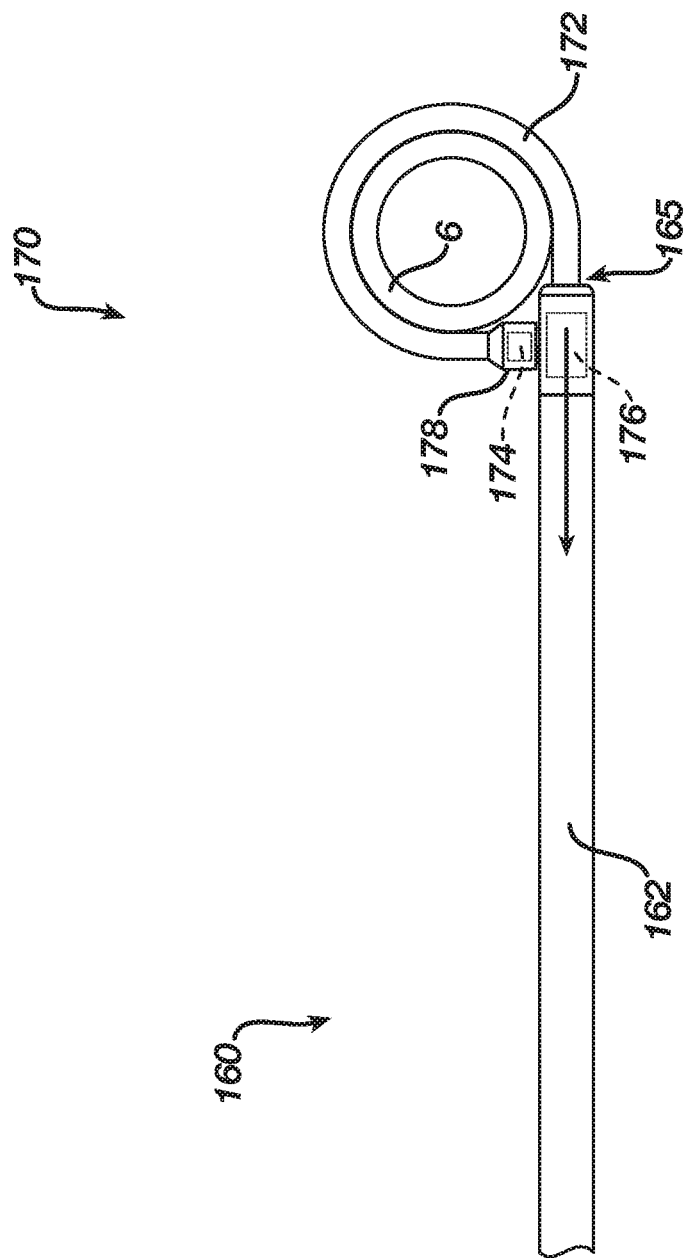
FIG. 14D depicts a top plan view of the end effector and shaft assembly of FIG. 10, where the end effector is in a retracted, closed, position while the end effector surrounds the lower esophageal sphincter.

Resilient flexible tube (172) is configured to transition between a closed position (e.g., as shown in FIGS. 14A, 14C, and 14D) and an opened position (e.g., as shown in FIG. 14B) in order to selectively encompass the LES (6). In the present example, first and second magnets (175, 176) may help ensure that distal tip (178) of resilient flexible tube (172) maintains contact with open distal end (165) of exterior sheath (162) even after the loop defined by resilient flexible tube (172) decreases in diameter as described below. In other words, first and second magnets (174, 176) may help ensure resilient flexible tube (172) remains in a closed position as the loop defined by resilient flexible tube (172) decreases in diameter due to the operator's manipulation of actuator (130). In other words, first and second magnets (174, 176) may help ensure resilient flexible tube (172) remains fully encompassed around the LES (6) such that resilient flexible tube (172) may suitably engage the outer diameter of the LES (6) during use of instrument (100).

Figure 11:
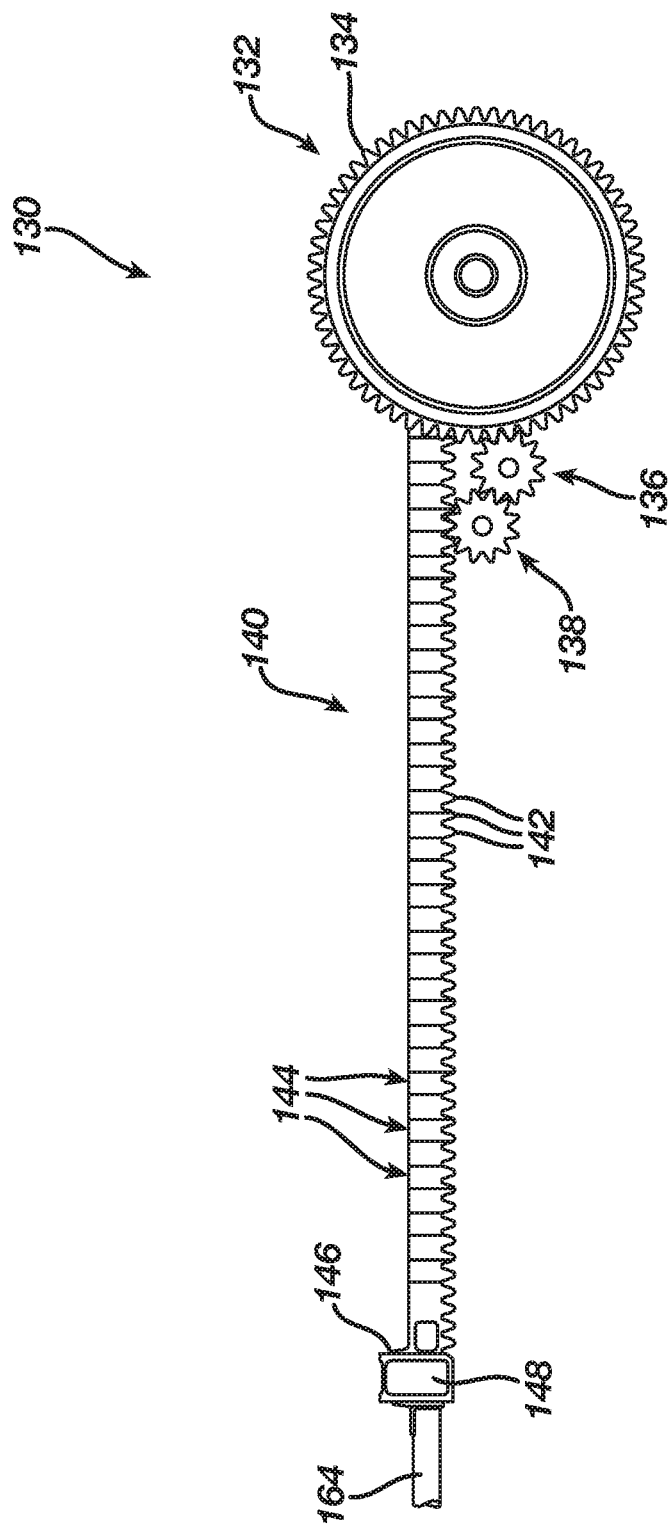
FIG. 11 depicts a side elevation view of the actuation assembly of FIG. 7.
Figure 12:
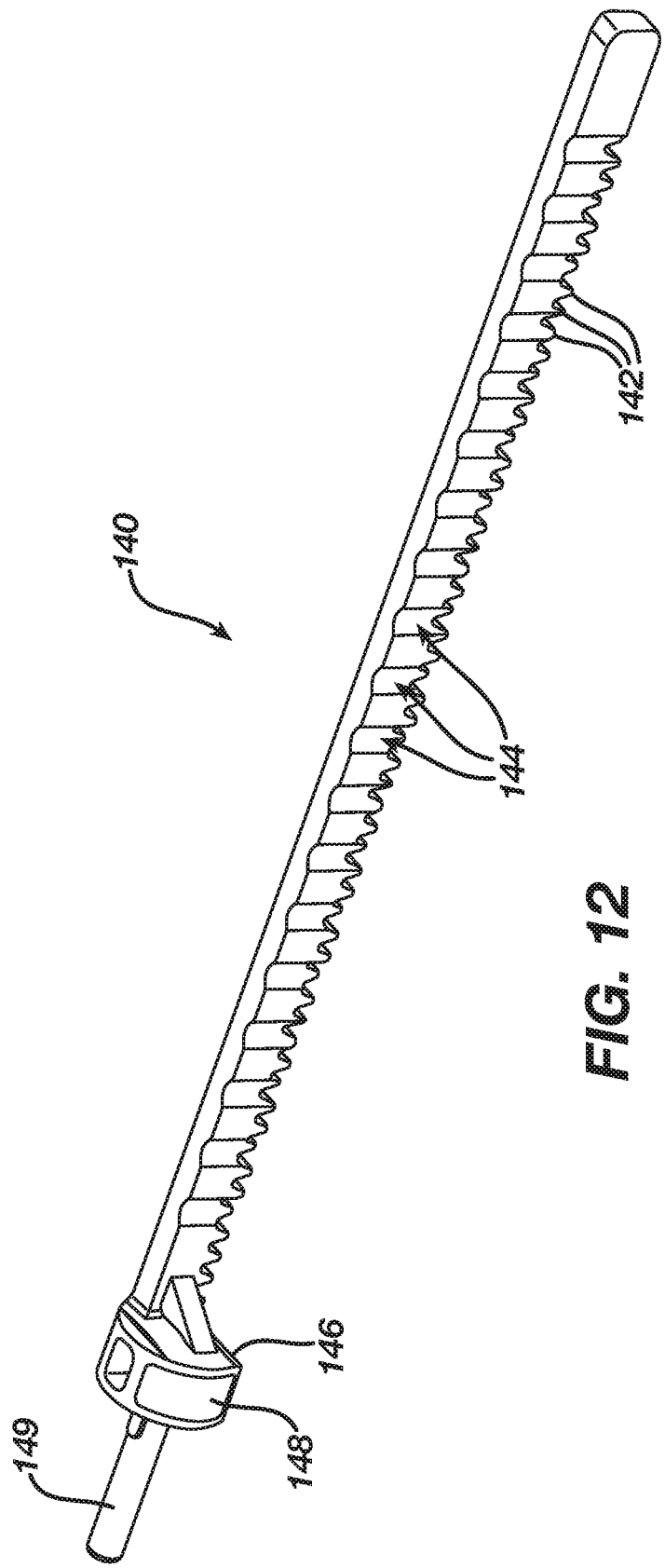
FIG. 12 depicts a perspective view of a rack of the actuation assembly of FIG. 7.

Actuator (130) is operable to decrease the diameter of the adjustable loop defined by resilient flexible tube (172) until resilient flexible tube (172) sufficiently engages the outer diameter of the LES (6) (as shown in FIG. 14D). FIG. 11 shows the components of actuator (130) that are utilized to accomplish the adjustment of the loop defined by resilient tube (172). In this example, actuator (130) includes a drive wheel (132), a pair of idler gears (136, 138), and a rack (140). Drive wheel (132) includes a set of teeth (134) that are exposed relative to housing (112) of handle assembly (102), as best seen in FIGS. 3-5. Thus, when an operator grasps grip portion (110), the operator's thumb may engage teeth (134) and thereby rotate drive wheel (132) relative to housing (112) in order to drive actuator (130). Idler gear (136) meshes with teeth (134) of drive wheel (132), such that rotation of drive wheel (132) rotates idler gear (136). Idler gear (136) meshes with idler gear (138), such that rotation of idler gear (136) rotates idler gear (138). Idler gear (138) meshes with teeth (142) of rack (140), such that rotation of idler gear (138) causes longitudinal translation of rack (140). As shown in FIG. 12, rack (140) includes a distally projecting prong (149). The proximal end of inner shaft (164) is fixedly secured to prong (149), such that translation of rack (140) causes translation of inner shaft (164).

Thus, actuator (130) is operable to convert rotary motion of drive wheel (132) into longitudinal motion of inner shaft (164). As inner shaft (164) translates distally, the diameter of the loop defined by resilient flexible tube (172) increases. As inner shaft (164) translates proximally, the diameter of the loop defined by resilient flexible tube (172) decreases. In other words, as shown between FIGS. 14C-14D, which will be described in greater detail below, movement of resilient flexible tube (172) relative to exterior sheath (162) affects the dimension of the loop defined by resilient flexible tube (172). In particular, the loop defined by tube (172) may become larger in response to distal rotation of drive wheel (132); while the loop defined by tube (172) may become smaller in response to proximal rotation of drive wheel (132). The size of the loop defined by resilient flexible tube (172) may be determined from the longitudinal position of indicator (146) on actuator (130) relative to windows (152) and the adjacent markings on handle assembly (102). In the present example, the size of drive wheel (132) and gears (136, 138) is such that the longitudinal motion of inner shaft (164) has an approximately 1:1 relationship with rotation of drive wheel (132). In some other versions, drive wheel (132)

and gears (136, 138) may be configured to scale (e.g., amplify or reduce) the longitudinal motion of inner shaft (164) relative to the rotary motion of drive wheel (132).

As best seen in FIGS. 11-12, the distal portion of rack (140) includes a flange (146) with an indicator (148) fixedly secured on flange (146). By way of example only, indicator (148) may take the form of a brightly colored strip or some other readily discernible visual feedback feature. Indicator (148) is positioned to be visible through windows (152) of housing (112) as actuator (130) is operated to translate rack (140) through the operational range of motion of rack (140). The operator may thus visually observe the location of indicator (148) through windows (152) and the adjacent markings to readily ascertain the longitudinal position of rack (140) relative to housing (112). This longitudinal position of rack (140) relative to housing (112) will be further indicative of the diameter of the loop defined by resilient flexible tube (172). This diameter of the loop defined by resilient flexible tube (172) may further indicate the diameter of the LES (6) of the patient at hand, such that the operator may visually observe the location of indicator (148) through windows (152) and the adjacent markings to readily ascertain the diameter of the LES (6) of the patient at hand. This information may enable the operator to determine the size of a device to install around the LES (6) and/or to make any other determination(s) that may be pertinent to the treatment of the patient. For example, if indicator (148) is aligned within with a window (152) marked with a "15" when end effector (170) sufficiently engages the outer diameter of the LES (6), a corresponding size "15" implant may be used in conjunction with that measured LES (6).

While actuator (130) of the present example is driven by drive wheel (132), other versions of actuator (130) may be driven by some other kind of user input feature. For instance, some variations of actuator (130) may be driven by a slider that translates longitudinally relative to housing (112). In some such versions, the slider may be directly secured to rack (140). In some other versions, the slider may be coupled to rack (140) via one or more pinions, such that the slider includes a rack that engages a pinion to rotate the pinion, with the resulting pinion rotation being converted to longitudinal motion of rack (140). As another merely illustrative example, drive wheel (132) may be replaced with a pivoting lever or rocker arm. Again, one or more pinions may be used to convert the pivotal motion of the lever or rocker arm into longitudinal motion of rack (140). Other suitable variations will be apparent to those skilled in the art in view of the teachings herein. It should also be understood that any of these variations may still present the single-handed operability of instrument (100), such that the operator may still manipulate the user input feature for actuator (130) with a thumb (or other finger) of the same hand that grasps grip portion (110).

Figure 13:
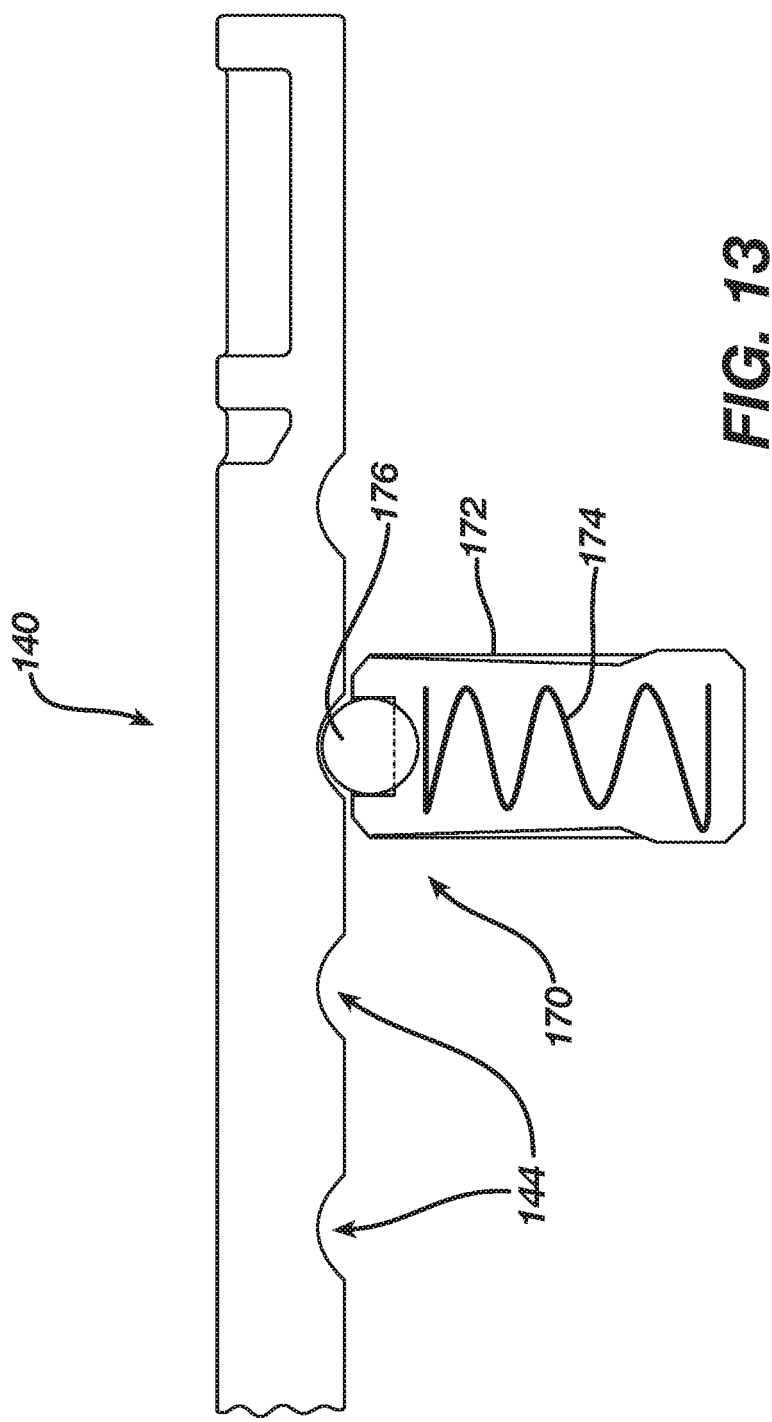
FIG. 13 depicts top plan view of a detent assembly engaged with the rack of FIG. 12.

As also shown in FIGS. 11-13, one side of rack (140) includes a longitudinally spaced array of lateral recesses (144). As shown in FIG. 13, recesses (144) are sized and positioned to receive a ball (176) of a detent assembly (170). Detent assembly (170) of this example includes a housing (172) with a resilient member (174). Housing (172) is fixedly secured to housing (112), such that housing (172) remains stationary within handle assembly (102) during operation of instrument (100). Resilient member (174) is in the form of a coil spring in this example, though resilient member (174) may instead be in the form of a leaf spring or have any other configuration as will be apparent to those skilled in the art in view of the teachings herein. Resilient member (174) is configured to resiliently urge ball (176) toward rack (140); while housing (172) is configured to guide and support ball (176). When rack (140) is positioned to receive ball (176) in one of recesses (144), ball (176) will seat in recess (144) as shown in FIG. 13.

When ball (176) is seated in recess (144), the cooperation between ball (176) and recess (144) will sufficiently maintain the longitudinal position of rack (140) relative to housing (112), such that the operator may readily obtain a visual reading of the location of indicator (148) through windows (152) and the adjacent markings. Cooperation between ball (176) and recess (144) will prevent inadvertent movement of rack (140) relative to housing (112), including when the operator disengages their thumb (or other finger) from drive wheel (132). However, ball (176) and recess (144) will still allow the operator to intentionally adjust the longitudinal position of rack (140) relative to housing (112) by driving drive wheel (132) as described above. Detent assembly (170) thus substantially maintains the longitudinal position of rack (140) relative to housing (112) while still permitting intentional adjustments of the longitudinal position of rack (140) relative to housing (112). Those skilled in the art will recognize that detent assembly (170) will permit both distal and proximal translation of rack (140), such that detent assembly (170) serves as a bi-directional translation resistance feature. Those skilled in the art will also recognize that detent assembly (170) is just one merely illustrative example of a form that a bi-directional translation resistance feature may take. Other suitable components that may be used to form a similarly functioning bi-directional translation resistance feature will be apparent to those skilled in the art in view of the teachings herein.

In the present example, the distance between recesses (144) corresponds with the distance between windows (152). Indicator (148) is positioned such that, each time ball (176) is seated in a given recess (144), indicator (148) will be centered within a corresponding window (152). Thus, in addition to resisting translation of rack (140) when rack (140) is at certain predetermined longitudinal positions, detent assembly (170) ensures that indicator (148) is meaningfully positioned with respect to windows (152) when detent assembly (170) arrests translation of rack (140). In other words, when ball (176) and recess (144) cooperate to arrest translation of rack (140), indicator (148) will be positioned relative to windows (152) to provide a very clear reading to the operator, preventing potential confusion as to whether indicator (148) is more accurately visible through one window (152) or another window (152). The position of indicator (148) relative to windows (152) will be discrete and binary. In addition to providing resistance to translation of rack (140) when rack (140) is at certain predetermined longitudinal positions, and ensuring that indicator (148) is appropriately centered within a window (152) when translation of rack (140) is arrested, detent assembly (170) may provide the operator with tactile and/or audible feedback indicating when rack (140) has reached a position where indicator (148) is appropriately centered within a window (152).

FIGS. 14A-14D show an exemplary use of sizing instrument (100). First, as shown in FIG. 14A, an operator may insert end effector (170) and a distal portion of shaft assembly (160) into a patient laparoscopically such that resilient flexible tube (172) is adjacent to the LES (6). During initial insertion of end effector (170) into the patient, flexible tube (172) may be deformed to a straight configuration in order to enable flexible tube (172) to freely pass through a cannula of a trocar or some other passageway into the patient. By way of example only, flexible tube (172) may be contained within exterior sheath (162), with a proximal edge of distal tip (178) abutting a distal edge of distal end (165), while end effector (170) is being inserted into the patient. As another merely illustrative example, the operator may grasp flexible tube (172) and substantially straighten flexible tube (172) to assist in feeding flexible tube (172) through a passageway, without necessarily retracting inner shaft (164) to a proximal-most position while inserting end effector (170) into the patient.

As shown in FIG. 14A, after end effector (170) has been inserted into the patient, end effector (170) is positioned near the LES (6). As shown, resilient flexible tube (172) is in a closed position at this stage. Actuator (130) is in a state where inner shaft (164) is in a distal-most position, such that resilient flexible tube (172) forms the largest loop. To the extent that inner shaft (164) was at a proximal-most position while end effector (170) was being inserted into the patient, actuator (130) may be manipulated to advance inner shaft (164) distally in order to achieve the configuration shown in FIG. 14A.

Next, as shown in FIG. 14B, the operator may grasp and pull a portion of resilient flexible tube (172) in order to overcome the biasing force of both tube (172) and magnets (174, 176) to transition resilient flexible tube (172) from the closed position to the opened position. In the present example, the operator may use a conventional grasping instrument (50) to pull tube (172) into the opened position. Alternatively, any other suitable instrument may be used as would be apparent to those skilled in the art in view of the teachings herein. With resilient flexible tube (172) in the opened position, the operator may adjust the position of end effector (170) such that the LES (6) is next to open distal end (165) of exterior sheath (162).

Next, as shown in FIG. 14C, the operator may release resilient flexible tube (172) from grasping instrument (50), such that tube (172) resiliently returns to the closed position. Magnetic attraction between magnets (174, 176) may further ensure that distal tip (178) of tube (172) appropriately engages distal end (165) of exterior sheath (162). At this point, the LES (6) is encompassed by resilient flexible tube (172). However, tube (172) is not yet suitably engaged with the LES (6) to the point where feedback feature (150) may be observed to measure the outer diameter of the LES (6).

With resilient flexible tube (172) properly encompassing the LES (6) in the closed position, the operator may manipulate actuator (130) to retract flexible tube (172) proximally to the point where flexible tube (172) is in full contact with the LES (6) as shown in FIG. 14D. At this point in time, the operator may visually observe the position of indicator (148) relative to windows (152) and the adjacent markings in order to determine the proper size for an implant.

After the measurement of the LES (6) attained through observation of feedback feature (150) as described above, the operator may remove instrument (100) from the patient through any suitable technique that would be apparent to those skilled in view of the teachings herein. For example, the operator may use grasping instrument (50) to grasp tube (172) and thereby transition tube (172) to the opened position, dissociate tube (172) from the LES (6), manipulate actuator (130) to retract tube (172) into exterior sheath (162), and then remove instrument (100) from the patient. Alternatively, the operator may begin by manipulating actuator (130) to retract tube (172) into exterior sheath (162), to the point where a proximal edge of distal tip (178) abuts a distal edge of distal end (165), and then remove instrument (100) from the patient.

It should be understood from the foregoing that, by utilizing instrument (100) as described above, and observing the measured size of the LES via feedback feature (150), the operator may utilize the measurement of the LES (6) to select an implant that is most appropriate for the patient at hand, to modify an implant so that the implant is at the most appropriate configuration for the patient at hand, and/or for any other purposes.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, the apparatus comprising: (a) a handle assembly, wherein the handle assembly comprises: (i) a handle body, and (ii) an actuator comprising a first rotary member, wherein the first rotary member is rotatable relative to the handle body, wherein the first rotary member is configured to be driven by a finger of a hand that grasps the handle body; (b) a shaft assembly extending distally from the handle assembly, wherein the shaft assembly comprises: (i) an external sheath fixed to the handle body, and (ii) an inner shaft coupled to the actuator, wherein the inner shaft is configured to slide longitudinally relative to the external sheath in response to rotation of the first rotary member relative to the handle body; and (c) an end effector configured to encompass a bodily lumen, wherein the end effector comprises: (i) a flexible member comprising a distal tip, wherein the flexible member extends distally from the inner shaft, (ii) a first coupling element fixed to the distal tip of the flexible member, and (iii) a second coupling element fixed to the external sheath, wherein the first and second coupling elements are configured to be magnetically attracted to each other, wherein the first and second coupling elements are biased toward each other such that the flexible member defines an adjustable loop, wherein the actuator is operable to adjust the size of the loop in response to movement of the first rotary member.

Example 2

The apparatus of Example 1, wherein the handle assembly defines a plurality of windows.

Example 3

The apparatus of Example 2, further comprising an indicator, wherein the indicator is configured to move relative to the windows in response to movement of the inner shaft relative to the handle assembly, wherein the indicator is positioned to be viewable through the windows of the handle assembly.

Example 4

The apparatus of any one or more of Examples 1 through 3, wherein the actuator further comprises a rack coupled with the inner shaft, wherein the rack is configured to translate in response to rotation of the first rotary member.

Example 5

The apparatus of Example 4, wherein the actuator further comprises a second rotary member coupled with the rack and with the first rotary member, wherein the second rotary member is configured to communicate rotation of the first rotary member to the rack.

Example 6

The apparatus of any one or more of Examples 4 through 5, further comprising an indicator secured to the rack, wherein the handle assembly defines a plurality of windows, wherein the indicator is configured to move relative to the windows in response to movement of the inner shaft relative to the handle assembly, wherein the indicator is positioned to be viewable through the windows of the handle body.

Example 7

The apparatus of any one or more of Examples 1 through 6, further comprising a bi-directional translation resistance feature, wherein the bi-directional translation resistance feature is configured to permit distal and proximal translation of the inner shaft relative to the external sheath, wherein the bi-directional translation resistance feature is further configured to restrict translation of the inner shaft relative to the external sheath at a plurality of predetermined longitudinal positions.

Example 8

The apparatus of Example 7, wherein the bi-directional translation resistance feature comprises a detent assembly.

Example 9

The apparatus of Example 8, wherein the detent assembly comprises a resiliently biased ball.

Example 10

The apparatus of Example 9, wherein the actuator comprises a series of recesses configured to receive the ball.

Example 11

The apparatus of Example 10, wherein the actuator further comprises a rack coupled with the inner shaft, wherein the rack defines the recesses.

Example 12

The apparatus of any one or more of Examples 7 through 11, further comprising an indicator, wherein the handle assembly defines a plurality of windows, wherein the indicator is configured to move relative to the windows in response to movement of the inner shaft relative to the handle assembly, wherein the indicator is positioned to be viewable through the windows of the handle assembly.

Example 13

The apparatus of Example 12, wherein the plurality of predetermined longitudinal positions correspond with respective positions where the indicator is centered within the windows.

Example 14

The apparatus of any one or more of Examples 1 through 13, wherein the shaft assembly is rigid.

Example 15

The apparatus of any one or more of Examples 1 through 14, wherein the shaft assembly is nonferrous.

Example 16

The apparatus of any one or more of Examples 1 through 15, wherein the first coupling element comprises a magnet.

Example 17

The apparatus of Example 16, wherein the second coupling element comprises a magnet.

Example 18

An apparatus, the apparatus comprising: (a) a handle assembly, wherein the handle assembly comprises: (i) a handle body, and (ii) an actuator, wherein the actuator comprises a user input feature that is configured to be driven by a finger of a hand that grasps the handle body; (b) a shaft assembly extending distally from the handle assembly, wherein the shaft assembly comprises: (i) an external sheath fixed to the handle body, and (ii) an inner shaft coupled to the actuator, wherein the inner shaft is configured to slide longitudinally relative to the external sheath in response to actuation of the actuator; (c) a bi-directional translation resistance feature, wherein the bi-directional translation resistance feature is configured to permit distal and proximal translation of the inner shaft relative to the external sheath, wherein the bi-directional translation resistance feature is further configured to restrict translation of the inner shaft relative to the external sheath at a plurality of predetermined longitudinal positions; and (d) an end effector configured to encompass a bodily lumen, wherein the end effector comprises: (i) a flexible member comprising a distal tip, wherein the flexible member extends distally from the inner shaft, (ii) a first coupling element fixed to the distal tip of the flexible member, and (iii) a second coupling element fixed to the external sheath, wherein the first and second coupling elements are configured to be magnetically attracted to each other, wherein the first and second coupling elements are biased toward each other such that the flexible member defines an adjustable loop, wherein the actuator is operable to adjust the size of the loop in response to movement of the first rotary member.

Example 19

The apparatus of Example 18, wherein the user input feature comprises a rotary drive wheel.

Example 20

An apparatus, the apparatus comprising: (a) a handle assembly, wherein the handle assembly comprises: (i) a handle body, (ii) a first set of windows positioned along a first side of the body, the windows of the first set being longitudinally spaced apart from each other, (iii) a second set of windows positioned along a second side of the body, the windows of the second set being longitudinally spaced apart from each other, and (iv) an actuator, wherein the actuator comprises a user input feature that is configured to be driven by a finger of a hand that grasps the handle body; (b) a shaft assembly extending distally from the handle assembly, wherein the shaft assembly comprises: (i) an external sheath fixed to the handle body, and (ii) an inner shaft coupled to the actuator, wherein the inner shaft is configured to slide longitudinally relative to the external sheath in response to actuation of the actuator; (c) an indicator, wherein the indicator is configured to move relative to the first set of windows and relative to the second set of windows in response to movement of the inner shaft relative to the handle assembly, wherein the indicator is positioned to be viewable through the first and second sets of windows of the handle assembly; and (d) an end effector configured to encompass a bodily lumen, wherein the end effector comprises: (i) a flexible member comprising a distal tip, wherein the flexible member extends distally from the inner shaft, (ii) a first coupling element fixed to the distal tip of the flexible member, and (iii) a second coupling element fixed to the external sheath, wherein the first and second coupling elements are configured to be magnetically attracted to each other, wherein the first and second coupling elements are biased toward each other such that the flexible member defines an adjustable loop, wherein the actuator is operable to adjust the size of the loop in response to movement of the first rotary member.

IV. MISCELLANEOUS

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, the apparatus comprising:
   (a) a handle assembly, wherein the handle assembly comprises:
      (i) a handle body including a plurality of windows positioned along a first side of the handle body, the plurality of windows being longitudinally spaced apart from each other, and
      (ii) an actuator comprising a first rotary member, wherein the first rotary member is rotatable relative to the handle body, wherein the first rotary member is configured to be driven by a finger of a hand that grasps the handle body;
   (b) a shaft assembly extending distally from the handle assembly, wherein the shaft assembly comprises:
      (i) an external sheath fixed to the handle body,
      (ii) an inner shaft coupled to the actuator, wherein the inner shaft is configured to slide longitudinally relative to the external sheath in response to rotation of the first rotary member relative to the handle body, and
      (iii) an indicator, wherein the indicator is configured to move relative to the plurality of windows in response to movement of the inner shaft relative to the handle body, wherein longitudinal spacing of the windows of the plurality of windows is configured to indicate a longitudinal relationship between the indicator and the external sheath, wherein the indicator is positioned to be viewable through the plurality of windows of the handle body; and
   (c) an end effector configured to encompass a bodily lumen, wherein the end effector comprises:
      (i) a flexible member comprising a distal tip, wherein the flexible member extends distally from the inner shaft,
      (ii) a first coupling element fixed to the distal tip of the flexible member, and
      (iii) a second coupling element fixed to the external sheath, wherein the first and second coupling elements are configured to be magnetically attracted to each other, wherein the first and second coupling elements are biased toward each other such that the flexible member defines an adjustable loop, wherein the actuator is operable to adjust the size of the loop in response to movement of the first rotary member, wherein the indicator and the windows of the plurality of windows are configured to cooperate to indicate the size of the adjustable loop.

2. The apparatus of claim 1, wherein the plurality of windows defines a first plurality of windows, wherein the handle assembly further defines a second plurality of windows, wherein the indicator and the windows of the second plurality of windows are configured to cooperate to indicate the size of the adjustable loop, the second plurality of windows being positioned on an opposing side of the handle body from the first plurality of windows.

3. The apparatus of claim 1, wherein the actuator further comprises a rack coupled with the inner shaft, wherein the rack is configured to translate in response to rotation of the first rotary member.

4. The apparatus of claim 3, wherein the actuator further comprises a second rotary member coupled with the rack and with the first rotary member, wherein the second rotary member is configured to communicate rotation of the first rotary member to the rack.

5. The apparatus of claim 4, wherein the indicator is secured to the rack.

6. The apparatus of claim 1, further comprising a bi-directional translation resistance feature, wherein the bi-directional translation resistance feature is configured to permit distal and proximal translation of the inner shaft relative to the external sheath, wherein the bi-directional translation resistance feature is further configured to restrict translation of the inner shaft relative to the external sheath at a plurality of predetermined longitudinal positions.

7. The apparatus of claim 6, wherein the bi-directional translation resistance feature comprises a detent assembly.

8. The apparatus of claim 7, wherein the detent assembly comprises a resiliently biased ball.

9. The apparatus of claim 8, wherein the actuator comprises a series of recesses configured to receive the ball.

10. The apparatus of claim 9, wherein the actuator further comprises a rack coupled with the inner shaft, wherein the rack defines the recesses.

11. The apparatus of claim 6, wherein the plurality of predetermined longitudinal positions correspond with respective positions where the indicator is centered within the windows.

12. The apparatus of claim 1, wherein the shaft assembly is rigid.

13. The apparatus of claim 1, wherein the shaft assembly is nonferrous.

14. The apparatus of claim 1, wherein the first coupling element comprises a magnet.

15. The apparatus of claim 14, wherein the second coupling element comprises a magnet.

16. An apparatus, the apparatus comprising:
(a) a handle assembly, wherein the handle assembly comprises:
(i) a handle body, including a plurality of windows positioned along a first side of the handle body, the plurality of windows being longitudinally spaced apart from each other, and
(ii) an actuator, wherein the actuator comprises a user input feature that is configured to be driven by a finger of a hand that grasps the handle body;
(b) a shaft assembly extending distally from the handle assembly, wherein the shaft assembly comprises:
(i) an external sheath fixedly secured to the handle body,
(ii) an inner shaft coupled to the actuator, wherein the inner shaft is configured to slide longitudinally relative to the external sheath and thus the handle body in response to actuation of the actuator, and
(iii) an indicator, wherein the indicator is configured to move relative to the plurality of windows in response to movement of the inner shaft relative to the handle body, wherein longitudinal spacing of the windows of the plurality of windows is configured to indicate a longitudinal relationship between the indicator and the external sheath, wherein the indicator is positioned to be viewable through the plurality of windows of the handle body; and
(c) a bi-directional translation resistance feature including a first resistance feature fixedly secured to the inner shaft and a second resistance feature fixedly secured to the handle body, wherein the second resistance feature is configured to permit distal and proximal translation of the first resistance feature and thus the inner shaft relative to the handle body while the user input feature is being driven, wherein the second resistance feature is further configured to maintain a longitudinal position of the first resistance feature and thus the inner shaft relative to the external sheath and thus the handle body at a plurality of predetermined longitudinal positions; and
(d) an end effector configured to encompass a bodily lumen, wherein the end effector comprises:
(i) a flexible member comprising a distal tip, wherein the flexible member extends distally from the inner shaft,
(ii) a first coupling element fixed to the distal tip of the flexible member, and
(iii) a second coupling element fixed to the external sheath, wherein the first and second coupling elements are configured to be magnetically attracted to each other, wherein the first and second coupling elements are biased toward each other such that the flexible member defines an adjustable loop, wherein the actuator is operable to adjust the size of the loop in response to movement of the user input feature.

17. The apparatus of claim 16, wherein the user input feature comprises a rotary drive wheel.

18. An apparatus, the apparatus comprising:
(a) a handle assembly, wherein the handle assembly comprises:
(i) a handle body,
(ii) a first set of windows positioned along a first side of the body, the windows of the first set being longitudinally spaced apart from each other,
(iii) a second set of windows positioned along a second side of the body, the windows of the second set being longitudinally spaced apart from each other, and
(iv) an actuator, wherein the actuator comprises a user input feature that is configured to be driven by a finger of a hand that grasps the handle body;
(b) a shaft assembly extending distally from the handle assembly, wherein the shaft assembly comprises:
(i) an external sheath fixed to the handle body, and
(ii) an inner shaft coupled to the actuator, wherein the inner shaft is configured to slide longitudinally relative to the external sheath in response to actuation of the actuator;
(c) an indicator, wherein the indicator is configured to move relative to the first set of windows and relative to the second set of windows in response to movement of the inner shaft relative to the handle assembly, wherein longitudinal spacing of the windows of the first set is configured to indicate a longitudinal relationship between the indicator and the external sheath, wherein the indicator is positioned to be viewable through the first and second sets of windows of the handle assembly; and (d) an end effector configured to encompass a bodily lumen, wherein the end effector comprises:
  (i) a flexible member comprising a distal tip, wherein the flexible member extends distally from the inner shaft,
  (ii) a first coupling element fixed to the distal tip of the flexible member, and
  (iii) a second coupling element fixed to the external sheath, wherein the first and second coupling elements are configured to be magnetically attracted to each other, wherein the first and second coupling elements are biased toward each other such that the flexible member defines an adjustable loop, wherein the actuator is operable to adjust the size of the loop in response to movement of the user input feature, wherein the indicator and the windows of the first set are configured to cooperate to indicate the size of the loop.

\* \* \* \* \*